US010968158B2

United States Patent
Xu

(10) Patent No.: US 10,968,158 B2
(45) Date of Patent: *Apr. 6, 2021

(54) METHOD OF DETERMINING THE INERTNESS OF MATERIALS FOR USE IN MONOMER PRODUCTION

(71) Applicant: Rohm and Haas Company, Collegeville, PA (US)

(72) Inventor: Jinsuo Xu, Fort Washington, PA (US)

(73) Assignee: Rohm and Haas Company, Philadelphia, PA (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/753,379

(22) PCT Filed: Aug. 22, 2016

(86) PCT No.: PCT/US2016/047975
§ 371 (c)(1),
(2) Date: Feb. 19, 2018

(87) PCT Pub. No.: WO2017/035054
PCT Pub. Date: Mar. 2, 2017

(65) Prior Publication Data
US 2018/0237373 A1    Aug. 23, 2018

Related U.S. Application Data

(60) Provisional application No. 62/209,004, filed on Aug. 24, 2015.

(51) Int. Cl.
| | | |
|---|---|---|
| *C07C 51/25* | (2006.01) | |
| *C07C 45/35* | (2006.01) | |
| *G01N 30/66* | (2006.01) | |
| *G01N 33/44* | (2006.01) | |
| *G01N 31/10* | (2006.01) | |
| *G01N 30/86* | (2006.01) | |

(52) U.S. Cl.
CPC ............ *C07C 51/252* (2013.01); *C07C 45/35* (2013.01); *G01N 30/8675* (2013.01); *G01N 31/10* (2013.01); *G01N 33/442* (2013.01)

(58) Field of Classification Search
CPC .... C07C 45/35; C07C 51/252; G01N 33/442; G01N 33/227; G01N 30/8675; G01N 31/10
See application file for complete search history.

(56) References Cited

U.S. PATENT DOCUMENTS

| | | | |
|---|---|---|---|
| 4,147,885 A * | 4/1979 | Shimizu | C07C 45/35 562/535 |
| 5,087,744 A | 2/1992 | Krabetz et al. | |
| 5,442,108 A | 8/1995 | Kawajiri et al. | |
| 5,532,199 A | 7/1996 | Watanabe et al. | |
| 5,959,143 A | 9/1999 | Sugi et al. | |
| 6,545,178 B1 | 4/2003 | Tanimoto et al. | |
| 6,762,148 B2 | 7/2004 | Ohishi et al. | |
| 7,518,015 B2 | 4/2009 | Cremer et al. | |
| 7,884,238 B2 | 2/2011 | Cremer et al. | |
| 2004/0077094 A1* | 4/2004 | Akporiaye | B01J 19/0046 506/11 |
| 2005/0137415 A1* | 6/2005 | Bogan, Jr. | C07C 51/215 558/320 |
| 2008/0253943 A1 | 10/2008 | Yoda et al. | |
| 2009/0042723 A1* | 2/2009 | Wang | B01J 23/002 502/312 |
| 2011/0137078 A1 | 6/2011 | Nakahara et al. | |
| 2013/0274508 A1 | 10/2013 | DeCourcy et al. | |
| 2013/0338396 A1* | 12/2013 | Lemonds | C07C 67/327 560/215 |
| 2014/0243554 A1* | 8/2014 | Han | C07C 51/215 562/512.2 |
| 2017/0260118 A1* | 9/2017 | Mimura | B08B 3/08 |
| 2018/0326322 A1* | 11/2018 | Kremerman | B01D 3/02 |

FOREIGN PATENT DOCUMENTS

EP    1714955 A1    10/2006

OTHER PUBLICATIONS

Acrylic Acid—PubChem (Acrylic Acid, PubChem, https://pubchem.ncbi.nlm.nih.gov/compound/Acrylic-acid#section=Safe-Storage, p. 49/84. Accessed 2019. (Year: 1997).*
Pillars Curriculum for Chemical Engineering—Multiple Reactions, University of Pittsburgh Department of Chemical and Petroleum Engineering, http://pillars.che.pitt.edu/student/slide.cgi?course_id=12&slide_id=53.0, p. 1/1 (Year: 2010).*
Bianchi et al. (Choosing the best diluent for a fixed catalytic bed: The case of Co hydrogenation, Catalysis Communications, 7, 2006, pp. 669-672) (Year: 2006) (Year: 2006).*
Khodakov et al. (Structure and Catalytic Properties of Supported Vanadium Oxides: Support Effects on Oxidative Dehydrogenation Reactions, Journal of Catalysis, 181, 1999, pp. 205-216) (Year: 1999) (Year: 1999).*

* cited by examiner

*Primary Examiner* — Benjamin R Whatley
*Assistant Examiner* — Jean Caraballo-Leon
(74) *Attorney, Agent, or Firm* — Brian L. Mutschler

(57) ABSTRACT

A method of determining the inertness of a material regarding the formation of heavy by-products during the reaction of propylene to acrolein and acrylic acid.

12 Claims, No Drawings

METHOD OF DETERMINING THE INERTNESS OF MATERIALS FOR USE IN MONOMER PRODUCTION

FIELD OF THE INVENTION

The invention relates to a process for preparing monomers, especially acrylic acid, and to a method of determining the inertness of materials used in that process.

BACKGROUND

Monomers, such as acrylic acid (AA), acrolein (ACR), and their corresponding derivatives, e.g., acrylic esters, are building blocks for many end-use products, such as coatings, adhesives, resins, plastics, and specialty chemicals. AA is currently produced commercially via the vapor phase oxidation of propylene over mixed metal oxide catalysts. In this 2-step process, ACR is first produced as an intermediate in a $1^{st}$ stage reactor (R1) by oxidation of propylene in the presence of steam, and is then further oxidized to AA in a $2^{nd}$ stage reactor (R2). Multiple shell and tube reactors are used, with catalyst packed inside the tubes and a heat transfer medium, such as HITEC® salt or Dowtherm™, circulating between the tubes to control the tube skin temperature. Tandem reactor and Single Reactor Shell (SRS) reactor are two typical types of reactors used. The R1 and R2 catalysts are packed into two separate tubes in tandem reactors, while in SRS reactors both the R1 and R2 catalysts are packed in one tube. The reactors may also have beds of inert materials, and catalysts may be diluted with inert materials and may be supported on inter materials. AA is recovered and purified by partial condensation and fractional distillation.

Maintaining a low tube inlet pressure is important in order to keep a high AA yield and to maintain a good production rate. However, the pressure drop (DP) across the catalyst bed normally increases over time due to the accumulation and deposition of particulates, including but not limited to catalyst fines, sublimed molybdenum oxides, and high boiling point byproducts, products, also called heavy by-products, or heavies, in the catalyst bed and before and/or after the catalyst bed, such as at the outlet of R1, the interstage region between R1 and R2, and the top or the bottom of R2.

Higher DP leads to higher reactor inlet pressure under constant feed rate. Consequently, higher inlet pressures result in lowered product yield, and the production rate of AA has to be compromised. When the production rate and/or yield drop to a point deemed uneconomical by the operator, the reactor will be shut down and packed with new catalyst(s). Such unscheduled shutdowns are expensive and disrupt the supply of AA.

As mentioned hereinabove, inert inorganic materials are widely used in the oxidation reactors, either in the "preheating" zone of the oxidation reactors, or at the end of the catalyst bed to cool down the products. Inert materials also may be used to dilute all or part of a catalyst bed in order to reduce the peak temperature of the bed. The inert materials mixed into catalyst bed are frequently referred to as "diluents."

Many examples of inert materials are reported in the literature. For example, U.S. Pat. No. 7,518,015 teaches that useful inert materials for the majority of the heterogeneously catalyzed gas phase partial oxidations of organic starting compounds are, for example, porous or nonporous aluminum oxides, silicon carbide, and silicates such as magnesium silicate or aluminum silicate, or steatite. US 2008/0253943 says that specific examples of diluents include compounds used for catalyst supports such as alumina, silicon carbide, silica, zirconium oxide, and titanium oxide. US 2013/0274508 discloses examples of stable, high surface area inert materials including 6 mm×6 mm aluminum raschig rings, 5 mm diameter silicon carbide spheres, 20 pore-per-inch open-cell ceramic foam, 16 mm diameter stainless steel Pall rings, and 13 mm MacroTrap™ Media 1.5.

The inert materials or diluents are not typically specified in terms of any property or performance in the prior art, except being generally described as substantially not reactive towards the reactant and/or the desired products.

The supports, or carriers, used in the preparation of oxidation catalysts, including those used for the partial oxidation of propylene or acrolein, frequently are described in term of "inertness." For example, in U.S. Pat. No. 7,884,238 teaches that useful support materials are the customary inert porous or non-porous aluminum oxides, silicon dioxide, thorium dioxide, zirconium dioxide, silicon carbide or silicates, such as magnesium silicate or aluminum silicate. In US 2011/0137078, inert materials are defined as having an activity of 20 or less when the activity of the catalyst powder for the applicable reaction is designated as 100 in the context of propylene oxidation. Examples of the material include α-alumina, silicon carbide, pumice, silica, zirconium oxide, and titanium oxide. The method of determining activity is not specified.

EP 1,714,955 discloses packing a solid acid in the oxidation reactor to suppress the deposition of catalyst inhibitors, such as organic solids, in a fixed bed the reactor. While the "solid acids" within certain a range of acid strength may be effective to suppress the deposition of organic solids in the reactor, it is not known whether these solid acids participate in the oxidation reaction or change the formation rate of organic solids. Furthermore, the activity of the solid acids is not related only to its acid strength, but also depends on the surface area of the solid acids. However, the surface area of the solid acids is not disclosed or specified. Therefore, the method disclosed in EP 1,714,955 cannot effectively be used to define the inertness of a solid material in propylene oxidation process.

In view of the deficiencies of the prior art, it would be desirable to have an improved method for determining the activity of a material towards the formation of high boiling point byproducts whose boiling point at 1 atm is at least 150° C., such as phthalic acid, in the vapor phase oxidation of propylene to acrolein and acrylic acid.

STATEMENT OF INVENTION

One aspect of the invention provides a process for determining the inertness of an inert material for use in monomer production comprising the steps of (a) providing a gaseous mixture (P1) comprising propylene, acrolein, and acrylic acid; (b) feeding P1 in the vapor phase at a pressure of from 1 to 1.5 atm to a fixed bed reactor tube containing the inert material having a bed temperature of from 200 to 450° C. for a contact time of at least 3 seconds, to produce a second mixture (P2) comprising acrolein and acrylic acid; (c) selectively condensing components of P2 having a boiling point at a pressure of 1 atm of at least 20° C.; (d) analyzing the condensed components for phthalic acid, acrolein, and acrylic acid; and (e) based on the analysis, determining the $PTA_{inert}$ of the inert material, wherein $PTA_{inert}$ is the ratio of the mass of phthalic acid in P2 to the total mass of acrolein and acrylic acid collected from P2.

In another aspect, the invention provides a process for selecting an inert material for use in monomer production comprising the steps of determining the inertness of two or more inert materials by carrying out the process described above to determine a $PTA_{inert}$ for each inert material, and selecting the inert material with the lowest $PTA_{inert}$.

Another aspect of the invention provides a process for determining the inertness of an inert material for use in monomer production comprising the steps of (a) oxidizing gaseous propylene in a fixed bed reactor tube in the presence of a mixed metal oxide catalyst to generate a gaseous mixture (P1) comprising propylene, acrolein, and acrylic acid, wherein the mixed metal oxide catalyst contains Mo and Bi; (b) feeding P1 in the vapor phase at a pressure of from 1 to 1.5 atm to a second fixed bed reactor tube containing an inert material having a bed temperature of from 200 to 450° C. for a contact time of at least 3 seconds, to produce a second product mixture (P2) comprising acrylic acid; (c) collecting P2 in a first trap (T1), having a trap skin temperature controlled at 0 to 5° C., wherein the uncondensed vapor from T1 is condensed in second, preferably stainless steel trap (T2), having a trap skin temperature controlled at 0 to 5° C., and wherein the uncondensed vapor from T2 is condensed in third stainless steel trap (T3), having a trap skin temperature controlled at from −60 to −80° C., and wherein each trap contains a solvent, preferably isopropanol, and a polymerization inhibitor, preferably hydroquinone or phenothiazine; (d) analyzing the uncondensed vapor from T3 for propylene, $O_2$, $N_2$, CO, and $CO_2$; (e) analyzing the condensed vapor from each trap for phthalic acid, acrolein and acrylic acid; and (f) based on the analysis, determining the $PTA_{inert}$ of the inert material, wherein $PTA_{inert}$ is the ratio of the mass of phthalic acid in P2 to the total mass of acrolein and acrylic acid collected from P2.

DETAILED DESCRIPTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "heavy by-products" means compounds, such as benzoic acid, phthalic acid, isophthalic acid, terephthalic acid, and benzene-1,2,4-tricarboxylic acid, having a boiling point above 150° C. at a pressure of 1 atmosphere.

As used herein, the term "ppm" means part per million by weight.

As used herein, the use of the term "(meth)" followed by another term such as acrylate refers to both acrylates and methacrylates. For example, the term "(meth)acrylate" refers to either acrylate or methacrylate; the term "(meth) acrylic" refers to either acrylic or methacrylic; and the term "(meth)acrylic acid" refers to either acrylic acid or methacrylic acid.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The disclosed method is a method of determining the inertness of a material regarding the formation of heavy by-products during the reaction of propylene to acrolein and/or acrylic acid. We found that as the run time of a reactor increased, flow restrictions developed at the interstage region in an SRS reactor or at the top of the $2^{nd}$ catalyst bed in a tandem reactor. Without being bound by any theory, we believe that heavy by-products and molybdenum oxide vapors likely condense and deposit in these "cold" spots, which then leads to DP increase.

A wide variety of materials have been proposed for use as inert materials in reactors and auxiliary equipment. Examples of these inert materials include, for example, porous or nonporous aluminum oxides, such as α-alumina, thorium dioxide, zirconium dioxide, zirconium oxide, titanium oxide, silica, pumice, silicon carbide, silicates such as magnesium silicate, aluminum silicate, steatite, silica, stable and high surface area inert materials including 6 mm×6 mm aluminum raschig rings, 5 mm diameter silicon carbide spheres, 20 pore-per-inch open-cell ceramic foam, 16 mm diameter stainless steel Pall rings, and 13 mm MacroTrap™ Media 1.5. In various embodiments of the invention, the inert material employed in the production of the desired monomer is preferred having lower or the lowest pthalic acid formed when different inert materials are compared.

Surprisingly, many so-called inert materials actually contribute to the generation of significant amounts of heavy by-products. The propensity of a material to generate such byproducts is not predictable from its activity, or lack thereof, toward major reactants and products.

In certain embodiments, other heavy byproducts alone or combined can be used in addition to or instead of phthalic acid to evaluate the inertness of the inert material. Such heavy byproducts include, for example, benzoic acid, isophthalic acid, terephthalic acid, and benzene-1,2,4-tricarboxylic acid.

The disclosed process operates a reactor system under conditions sufficient to produce the desired monomer. Selective oxidation processes for the production of acrylic acid and acrolein, and catalysts for use therein, are well-known to those skilled in the art; see, e.g., US 2013/0274508, the teachings of which relating to the production of acrylic acid and acrolein, and catalysts for use therein, are incorporated herein by reference. Similarly, selective oxidation processes for the production of methacrolein and methacrylic acid, and catalysts for use therein, are also well-known to those skilled in the art; see U.S. Pat. Nos. 5,087,744 and 5,532,199, the teachings of which relating to the production of methacrolein and mathacrylic acid, and catalysts for use therein, are incorporated herein by reference.

In one embodiment of the invention, when the desired monomer is acrylic acid, propylene is oxidized in a first stage reactor to produce a gaseous mixture (P1) comprising propylene, acrolein, and acrylic acid. In certain embodiments, P1 comprises from 0 to 0.5 mol. % propylene, from 0.1 to 1.0 mol. % acrylic acid, and from 1 to 10 mol. % acrolein. In certain embodiments, P1 is provided by oxidizing gaseous propylene in a fixed bed reactor tube in the presence of a mixed metal oxide catalyst. In certain embodiments, the mixed metal oxide catalyst contains Mo and Bi. P1 is then fed in the vapor phase to a second stage reactor containing an inert material having a bed temperature of from 200 to 450° C., preferably 250 to 350° C., for a contact time and at a pressure sufficient to produce a second product mixture (P2) comprising acrolein and acrylic acid. In one embodiment of the invention, the pressure in the second stage reactor is from 1 to 1.5 atm, and the contact time is at least 3 seconds. P2 is subjected to conditions sufficient to condense its components having a boiling point at a pressure of 1 atm of at least 20° C. The uncondensed vapor from is analyzed for propylene, $O_2$, $N_2$, CO, and $CO_2$ content. The condensed components are analyzed for phthalic acid, acrolein, and acrylic acid content. In certain embodiments, this procedure is repeated using a second stage reactor that contains a different inert material. The inert material selected for the production of the desired monomer has the lowest phthalic acid formed among these difference cases.

In certain embodiments, the oxidation process is vapor phase oxidation of acrolein to acrylic acid. In certain embodiments, the oxidation process is the vapor phase oxidation of isobutene and/or tert-butanol to methacrolein and methacrylic acid. In certain embodiments, the oxidation process is the vapor phase oxidation of a compound selected from isobutene, tert-butanol, and combinations thereof, to methacrolein and methacrylic acid. In certain embodiments, the oxidation process is the vapor phase oxidation of methacrolein to methacrylic acid.

The procedure can be employed for monomers, such as alpha, beta unsaturated carboxylic acids, such as acrylic monomers, such as (meth)acrylic acid, as well as unsaturated aldehydes, such as (meth)acrolein.

Some embodiments of the invention will now be described in detail in the following Examples.

EXAMPLES

Evaluation Method

Propylene oxidation to acrolein and acrylic acid is conducted in two stages. Oxidation of propylene is conducted in a $P^t$ reactor to generate the reaction intermediates similar to the effluent from a commercial $1^{st}$ stage reactor in a two-step propylene oxidation process to produce acrylic acid. 15 ml of a commercial $1^{st}$ stage catalyst available from Nippon Kayaku Co. is mixed with 15 ml of 1/8" Denstone® 57 beads, available from Saint-Gobain Norpro, Ohio, USA, before being loaded into a 1" OD stainless steel (SS) $1^{st}$ stage tube reactor (0.834" ID). The tube is heated to 367° C. in a clam-shell electrical furnace. The feed to the $1^{st}$ stage tube reactor is a mixture of 24.0 ml/min propylene, 211.6 ml/min air, 34.0 ml/min $N_2$, and 1.44 gram/h deionized water. The values of all gas flow rates are under standard temperature (0° C.) and standard pressure (1 atm) conditions. The water is injected by a syringe pump into a SS mixer vessel heated to 180° C. The other gases are controlled by mass flow controller. About 150 ml of inert material is loaded into a separate 1" OD×18" long SS tube, which serves as a $2^{nd}$ reactor tube residing in a clam-shell electrical furnace. The effluent from the $1^{st}$ stage reactor, designated as P1, is fed directly to the inert bed of the $2^{nd}$ reactor via a 1/4" SS transfer tube. Both reactors are vertically oriented and are in a downflow configuration, i.e., the feed is fed to the top of each reactor.

The product transfer tube between the reactors is heated by heating tape to 260° C. to prevent condensation of the reaction products, especially heavy by-products. The effluent from the $1^{st}$ stage reactor or from the $2^{nd}$ reactor is collected and analyzed periodically. The effluent first flows through a $1^{st}$ trap, designated T1, which is cooled by a recirculation chiller at 0-2° C. The gases escaping the $1^{st}$ trap flow through a $2^{nd}$ trap, designated T2, which is immersed in water/ice, and then a $3^{rd}$ trap, designated T3, which is immersed in dry ice/isopropanol mixture. The trap collection time is typically 3-4 hours. A polymerization inhibitor solution of 6 to12 grams is injected into each trap before sample collection to prevent polymer formation. 2% wt of hydroquinone in iso-propanol, or 1000 ppm of phenothiazine in iso-propanol, is used as inhibitor solution.

The off gas from T3 is analyzed on-line by a gas chromatograph (GC) equipped with a thermal conductivity detector and a 5 Å molecular sieve/silica gel column. The main gas components in the off gas typically include nitrogen, oxygen, unreacted propylene, carbon monoxide, and carbon dioxide. The liquids collected from T1 and T2 are combined into one sample, labeled as TS-12, before off-line analysis. The liquid collected from T3 is labeled as TS-3. The TS-12 and TS-3 samples are sent for off-line analysis by a GC equipped with flame ionization detector and a capillary column DB-FFAP 123-3232E obtainable from Agilent Technologies, USA. The amounts of major products, such as acrylic acid, acrolein, acetaldehyde, acetone, propionic acid, acetic acid are recorded.

The TS-12 and TS-3 samples are further analyzed for phthalic acid concentration using high performance liquid chromatography (HPLC). The HPLC instrument parameters are provided in Table 1.

TABLE 1

HPLC Instrumental Parameters

| | |
|---|---|
| Instrument: | Agilent 1200 Series Liquid Chromatograph |
| Column: | Hypersil GOLD PFP (Thermo Scientific) |
| Dimensions: | 4.6 × 250 mm, 5μ particle size |
| Column Temperature: | 25° C. |
| Injection Volume: | 2 μL |
| Column Flow Rate: | 0.96 mL/min |
| Solvent Composition Timetable: | |

| | | % A | % B |
|---|---|---|---|
| Solvent A = MilliQ water with 0.1% phosphoric acid | 0.0 min | 90 | 10 |
| | 16.0 min | 65 | 35 |
| Solvent B = acetonitrile (ACN) | 22.0 min | 45 | 55 |
| | 22.1 min | 90 | 10 |
| | 50.0 min | 90 | 10 |
| | 51.0 min | 90 | 10 |
| Detector: | Diode Array Detector | | |
| Monitor Signal: | 235 nm | | |
| Data Acquisition and Data Analysis: | Agilent ChemStation, version B.03.01 | | |

The phthalic acid standard material was obtained from Sigma-Aldrich. The initial stock standard solution is prepared in dimethyl sulfoxide (DMSO) solvent at various concentrations between 10-1000 ppm. The working standard solution is prepared by diluting 0.2 g of stock standard in 2 ml of acetonitrile. The working standard solution is filtered with a 0.45 μm syringe filter and is delivered to a 2 ml autosampler vial for injection into the HPLC.

The reactor temperature of the $1^{st}$ stage reactor is maintained at 367° C. to obtain a product mixture similar to that of a commercial $1^{st}$ stage reactor effluent. The composition of the effluent is analyzed by GC and the main components are listed in Table 2. The concentration of individual components may vary due to variation in experimental control or catalyst performance. It is recommended that P1 contains at least acrolein, acrylic acid, and propylene in order to be an effective feed to test the activity of the inert material loaded into the $2^{nd}$ stage reactor.

TABLE 2

Composition of the $1^{st}$ stage reactor effluent P1

| Component | Mole % |
|---|---|
| $CO_2$ | 0.892 |
| $C_3H_6$ | 0.217 |
| $O_2$ | 5.793 |
| Argon | 0.695 |
| $N_2$ | 67.368 |
| CO | 0.378 |
| $H_2O$ | 17.937 |
| Acetaldehyde | 0.073 |
| Acetone | 0.004 |
| Acrolein | 5.929 |
| Acetic Acid | 0.038 |
| Propionic Acid | 0.000 |
| Acrylic Acid | 0.676 |

The propylene conversion, yield of acrolein and acrylic acid, and relative amount of pthalic acid are calculated according to the equations below.

Propylene conversion (%)=(moles of propylene fed—moles of propylene unreacted)/moles of propylene fed.

Yield of acrolein & Acrylic Acid (%)=(moles of acrolein formed+moles of AA formed)/moles of propylene fed.

The relative total amount of pathalic acid from TS-12 and TS-3 samples verses the total amount of acrolein and AA formed is calculated according to the equations below:

$PTA_{inert}$ (ppm)=(mass of phthalic acid in TS-12 and TS-3 samples with inert loaded in $2^{nd}$ reactor tube)/(total mass of acrolein and AA in TS-12 and TS-3 samples with inert loaded in $2^{nd}$ reactor tube)*1,000,000.

Example 1

Evaluation of Inertness of Denstone®99 (Ex. 1)

The Evaluation Method was conducted with 165 ml of Denstone®99 ⅛" spheres, available from Saint Gobain Norpro, USA, loaded into the $2^{nd}$ stage reactor tube. The contact time based on the feed mixture of $1^{st}$ stage reactor was 33 seconds. The effluents from the $2^{nd}$ stage reactor were collected as described above and analyzed. The $2^{nd}$ stage reactor was controlled at 270 and 320° C. The propylene conversion, yield of "acrolein and AA," and phthalic acid are listed in Table 3. The data at 320° C. is the average of two samples.

Example 2

Evaluation of Inertness of SC5532 Silicon Carbide (Ex. 2)

The Evaluation Method was conducted with 185 ml of SC5532 silicon carbide 10 mm rings, available from Saint Gobain Norpro, USA, loaded in the $2^{nd}$ stage reactor tube. The contact time, based on the feed mixture of the $1^{st}$ stage reactor, was 37 seconds. The effluents from the $2^{nd}$ stage reactor were collected as described above and analyzed. The $2^{nd}$ stage reactor is controlled at 270 and 320° C. The propylene conversion, yield of "acrolein and AA," and phthalic acid are listed in Table 3. The data at 320° C. is the average of three samples.

Example 3

Evaluation of Inertness of LSA SA5218 Silica Alumina (Ex. 3)

The Evaluation Method was conducted with 160 ml of low surface area LSA SA5218 3-4 mm silica alumina spheres, available from Saint Gobain Norpro, USA, loaded in the $2^{nd}$ stage reactor tube. The contact time, based on the feed mixture of the $1^{st}$ stage reactor, was 32 seconds. The effluents from $2^{nd}$ stage reactor were collected as described above and analyzed. The $2^{nd}$ stage reactor is controlled at 270 and 320° C. The propylene conversion, yield of "acrolein and AA," and phthalic acid are listed in Table 3. The data at 320° C. is the average of two samples.

Example 4

Selection of Inert Material

The PTAmert of Examples 1-3 above are shown in Table 3.

TABLE 3

Change of Reactant Conversion, Product Yield, and Heavy By-product Formation with Different Inert Materials

| Experiment | Inert tested | Temperature of $2^{nd}$ reactor (° C.) | PP Conv. (%) | Yield of "acrolein + AA" (%) | PTA (ppm vs. combined acrolein and AA) |
|---|---|---|---|---|---|
| Ex. 1 | Denstone ® 99 | 270 | 96.8 | 85.2 | 166 |
|  |  | 320 | 96.9 | 86.7 | 148.5 |
| Ex. 2 | Silicon Carbide, SC5532 | 270 | 96.9 | 87.0 | 56 |
|  |  | 320 | 97.0 | 87.5 | 83 |
| Ex. 3 | Silica Alumina, LSA SA5218 | 270 | 96.6 | 92.8 | 55 |
|  |  | 320 | 96.7 | 90.4 | 63 |

The results in Table 3 show that the combined yield of "acrolein and AA" drops slightly after the product mixture flows through the Denstone®99 and the silicon carbide verses alumina SA5218, and the propylene conversion is comparable among the three different inert materials. Surprisingly, only the Denstone®99 significantly increases the amount of phthalic acid formation at both 270 and 320° C. verses the two other inert materials. Silica Alumina (LSA SA5218) will be preferred in the oxidation process when compared against Denstone®99 and Silicon Carbide (SC5532) due to its overall lower PTA (ppm).

The mechanism of phthalic acid formation is not understood. However, it is apparent, based on this data, that the PTA (ppm) of a solid material is not directly proportional to its activity toward reactant propylene, or the products acrolein and AA. The change of PTA (ppm) with temperature for a given solid material also appears to be unpredictable.

What is claimed is:

1. A process for determining the inertness of an inert material for use in monomer production comprising the steps of:
   (a) providing a gaseous mixture (P1) comprising propylene, acrolein, and acrylic acid;
   (b) feeding P1 in the vapor phase at a pressure from 1 to 1.5 atm to a fixed bed reactor tube containing the inert material having a bed temperature from 200 to 450° C. for a contact time of at least 3 seconds, to produce a second mixture (P2) comprising acrolein and acrylic acid;
   (c) selectively condensing components of P2 having a boiling point at a pressure of 1 atm of at least 20° C.;
   (d) analyzing the condensed components for phthalic acid, acrolein, and acrylic acid; and
   (e) based on the analysis, determining the $PTA_{inert}$ of the inert material, wherein $PTA_{inert}$ is the ratio of the mass of phthalic acid in P2 to the total mass of acrolein and acrylic acid collected from P2.

2. The process of claim 1, wherein the bed temperature in step (b) is from 250 to 350° C.

3. The process of claim 1, wherein the monomer production is vapor phase oxidation of propylene to acrolein and acrylic acid.

4. The process of claim 1, wherein the monomer production is vapor phase oxidation of acrolein to acrylic acid.

5. The process of claim 1, wherein the monomer production is vapor phase oxidation of isobutene and/or tert-butanol to methacrolein and methacrylic acid.

6. The process of claim 1, wherein the monomer production is vapor phase oxidation of methacrolein to methacrylic acid.

7. The process of claim 1, wherein P1 is provided by oxidizing gaseous propylene in a fixed bed reactor tube in the presence of a mixed metal oxide catalyst.

8. The process of claim 7, wherein the mixed metal oxide catalyst contains Mo and Bi.

9. A process for selecting an inert material for use in monomer production comprising the steps of determining the inertness of two or more inert materials by carrying out the process of claim 1 to determine a $PTA_{inert}$ for each inert material, and selecting the inert material with the lowest $PTA_{inert}$.

10. A process for determining the inertness of an inert material for use in monomer production comprising the steps of:
   (a) oxidizing gaseous propylene in a fixed bed reactor tube in the presence of a mixed metal oxide catalyst to generate a gaseous mixture (P1) comprising propylene, acrolein, and acrylic acid, wherein the mixed metal oxide catalyst contains Mo and Bi;
   (b) feeding P1 in the vapor phase at a pressure from 1 to 1.5 atm to a second fixed bed reactor tube containing an inert material having a bed temperature from 200 to 450° C. for a contact time of at least 3 seconds, to produce a second product mixture (P2) comprising acrylic acid;
   (c) collecting P2 in a first trap (T1), having a trap skin temperature controlled at 0 to 5° C., wherein the uncondensed vapor from T1 is condensed in second trap (T2), having a trap skin temperature controlled at 0 to 5° C., and wherein the uncondensed vapor from T2 is condensed in third stainless steel trap (T3), having a trap skin temperature controlled at from −60 to −80° C., and wherein each trap contains a solvent and a polymerization inhibitor;
   (d) analyzing the uncondensed vapor from T3 for propylene, O2, N2, CO, and CO2;
   (e) analyzing the condensed vapor from each trap for phthalic acid, acrolein and acrylic acid; and
   (f) based on the analysis, determining the $PTA_{inert}$ of the inert material, wherein $PTA_{inert}$ is the ratio of the mass of phthalic acid in P2 to the total mass of acrolein and acrylic acid collected from P2.

11. The process of claim 10, wherein each trap contains isopropanol.

12. The process of claim 10, wherein the polymerization inhibitor is selected from hydroquinone and phenothiazine.

* * * * *